United States Patent [19]

Carlson

[11] Patent Number: 4,810,884
[45] Date of Patent: Mar. 7, 1989

[54] APPARATUS AND METHOD TO DISTINGUISH BETWEEN OIL AND GAS COMBUSTION BY REMOTE OBSERVATION USING AN INFRARED SPECTROMETER

[75] Inventor: Ronald C. Carlson, Danbury, Conn.

[73] Assignee: The Perkin-Elmer Corporation, Norwalk, Conn.

[21] Appl. No.: 100,854

[22] Filed: Sep. 25, 1987

[51] Int. Cl.$^4$ .............................................. G01J 3/443
[52] U.S. Cl. .................................. 250/338.5; 250/339
[58] Field of Search ................. 250/339, 338 GA, 343

[56] References Cited

U.S. PATENT DOCUMENTS

| | | |
|---|---|---|
| 3,517,190 | 6/1970 | Astheimer ............................ 250/339 |
| 4,009,962 | 3/1977 | Lauer et al. .......................... 250/341 |
| 4,539,588 | 9/1985 | Ariessohn et al. ................... 250/330 |
| 4,549,080 | 10/1985 | Baskins et al. ....................... 250/343 |
| 4,560,873 | 12/1985 | McGowan et al. ................. 250/343 |

OTHER PUBLICATIONS

Williams et al., "Observations of Southern Stars with a New Infrared Photometer", vol. 96, 10/1976, pp. 184–188.

Primary Examiner—Janice A. Howell
Assistant Examiner—William F. Rauchholz
Attorney, Agent, or Firm—Thomas P. Murphy; Paul A. Fattibene; Edwin T. Grimes

[57] ABSTRACT

An apparatus and method for detecting and analyzing the emissions or effluents from gas or oil combustion so as to discriminate between them. A spectrometer detects the spectra of a combustion effluent or exhaust. Identifying features of carbon dioxide and water vapor are selected at predetermined wavenumbers. The ratio of the relative intensities of the identifying features of carbon dioxide and water vapor is then computed, which results in the discrimination between oil and gas effluents.

12 Claims, 4 Drawing Sheets

# APPARATUS AND METHOD TO DISTINGUISH BETWEEN OIL AND GAS COMBUSTION BY REMOTE OBSERVATION USING AN INFRARED SPECTROMETER

FIELD OF THE INVENTION

This invention relates generally to the remote detection of combustion emissions, and more particularly to an apparatus and method for remotely discriminating between oil and gas stack emissions using infrared spectroscopy.

BACKGROUND OF THE INVENTION

As energy costs and the need for tighter control of costs increase, the unauthorized use of gas creates mounting concern. Energy companies, in an effort to reduce this unauthorized use, have investigated possible solutions. Efforts have been made to determine the type of fuel burned from the emissions of the combustion. Typically, the plume of emissions emanating from a stack would be sampled. In order to sample these emissions, access to the stack is necessary. The samples taken are then analyzed to determine the type of fuel used. In most situations, the taking of samples is difficult due to the inaccessibility from the ground of stack emissions. This inaccessibility is sometimes exacerbated by uncooperative building owners or tenants.

It became necessary for energy companies to seek alternative solutions to their unauthorized gas use problems. Lasers could be used to remotely sense chemical compounds in the stack emissions. Laser systems tend to be complex and therefore costly. Additionally, laser systems, not being passive, result in health risks and potential injury from laser light. These remote detectors also tend to be unreliable and produce a high false alarm rate, a false alarm being an erroneous indication of gas combustion when in actuality none existed.

While the apparatus and methods used to distinguish between the combustion of oil and gas fuels have assisted energy companies somewhat in reducing the unauthorized use of gas, none could adequately identify gas combustion easily. Therefore, it became necessary to investigate other apparatus and methods for distinguishing between gas and oil combustion.

SUMMARY OF THE INVENTION

The present invention is directed to a remote sensing apparatus and method for discriminating between combustion emissions generated from the burning of gas or oil. An infrared spectrometer is used to detect the infrared spectral radiation emitted by the combustion effluents. Spectral data is gathered from the combustion effluents, or plume. The data gathered is mixed with unwanted signals introduced by highly varying background sources such as the sky, clouds, trees, walls of buildings, the hot smokestack and the atmosphere in front of and behind the plume. The removal of the time varying unwanted signals is accomplished with background suppression techniques to obtain the effluent spectra desired for analysis. Identifying features of the spectra corresponding to the relativistic quantity of carbon dioxide and water vapor are selected. These identifying features are used to establish a ratio of carbon dioxide and water vapor which is indicative of whether gas or oil was used for a fuel.

Accordingly, it is an objective of the present invention to detect the unauthorized use of gas.

It is a further objective of the present invention to provide an easy to use device for discriminating between the combustion effluents of gas and oil.

It is an advantage of the present invention that the unauthorized use of gas can be passively and remotely detected.

It is a further advantage of the present invention that the device can be made portable for easy transportation to individual sites.

It is a feature of the present invention that the ratio of carbon dioxide and water vapor is used to discriminate gas combustion plumes or effluents from oil combustion plumes or effluents.

It is a further feature of the present invention that standard hardware can be used with little modification, thereby resulting in lower cost.

These and other objects, advantages, and features will become readily apparent in view of the following more detailed description.

DETAILED DESCRIPTION OF THE PREFERRED EMBODIMENT

Figure 1:
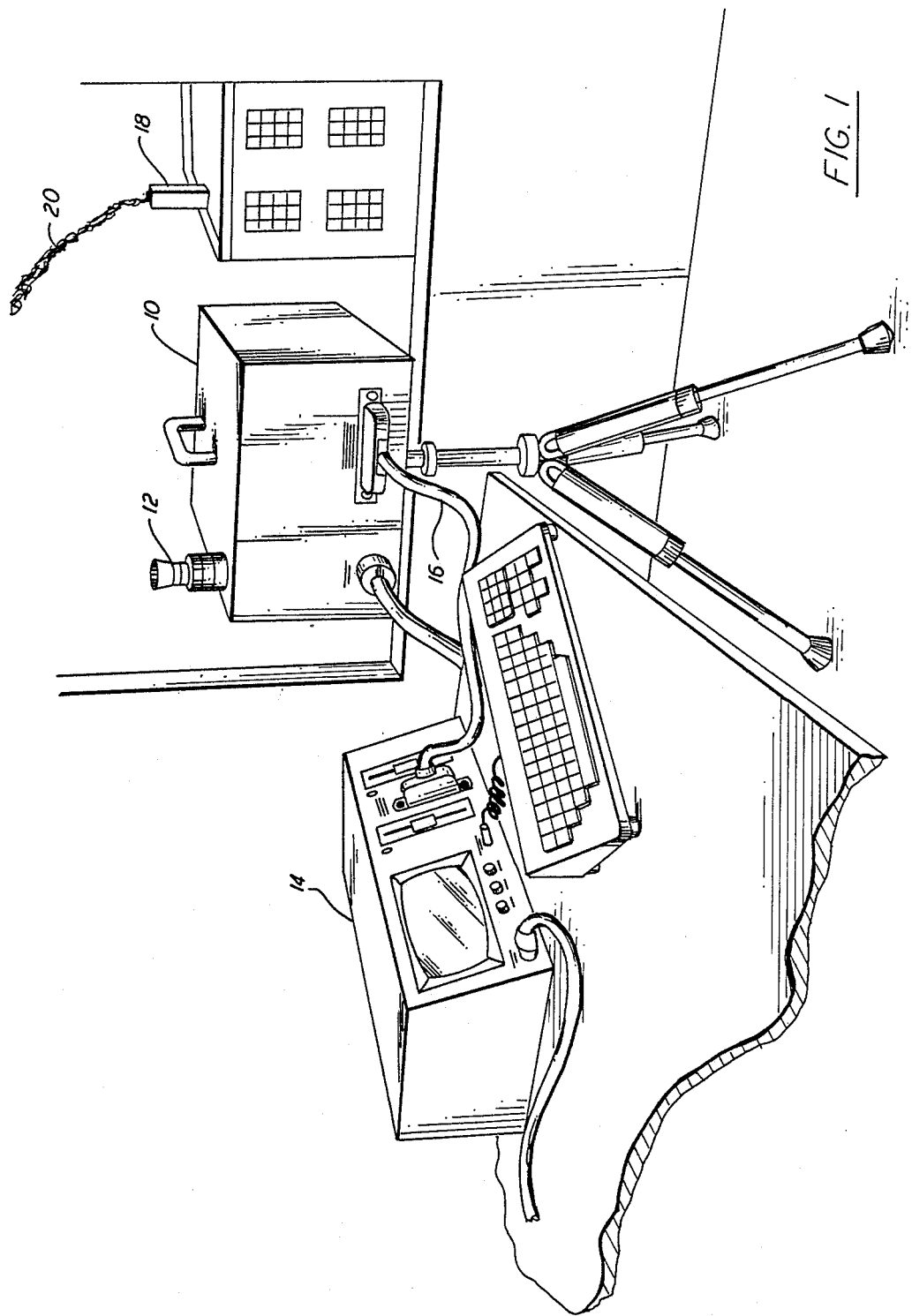
FIG. 1 is a representative illustration of the complete invention.

FIG. 1 illustrates the present invention. As is shown in FIG. 1, a spectrometer 10 is used to detect the infrared spectral radiation emitted by the effluents or plume 20. Spectrometer 10 can detect a broad spectral band, including the identifying spectral features used to discriminate between gas and oil combustion. Or, if desired, the spectrometer 10 can be designed to detect only predetermined narrow spectral bands centered about the identifying spectral features used to discriminate between gas and oil combustion. Spectrometer 10 can be any type of spectrometer such as a Fourier transform spectrometer, grating spectrometer, radiometer, etc. Eyepiece 12 is used to align the field of view of spectrometer 10 onto the effluent 20 emanating from stack 18. The spectral information obtained from spectrometer 10 is transmitted to computer 14 through communication cable 16. Computer 14 can store the predetermined carbon dioxide and water vapor identifying feature spectra for comparing it with the spectral band detected by spectrometer 10. The presence of the identifying feature spectra for carbon dioxide and water vapor can then be detected and measured by computer 14 so that their ratio can be calculated. Computer 14 then processes the spectral information, resulting in the discrimination between oil and gas combustion effluents.

Figure 2:
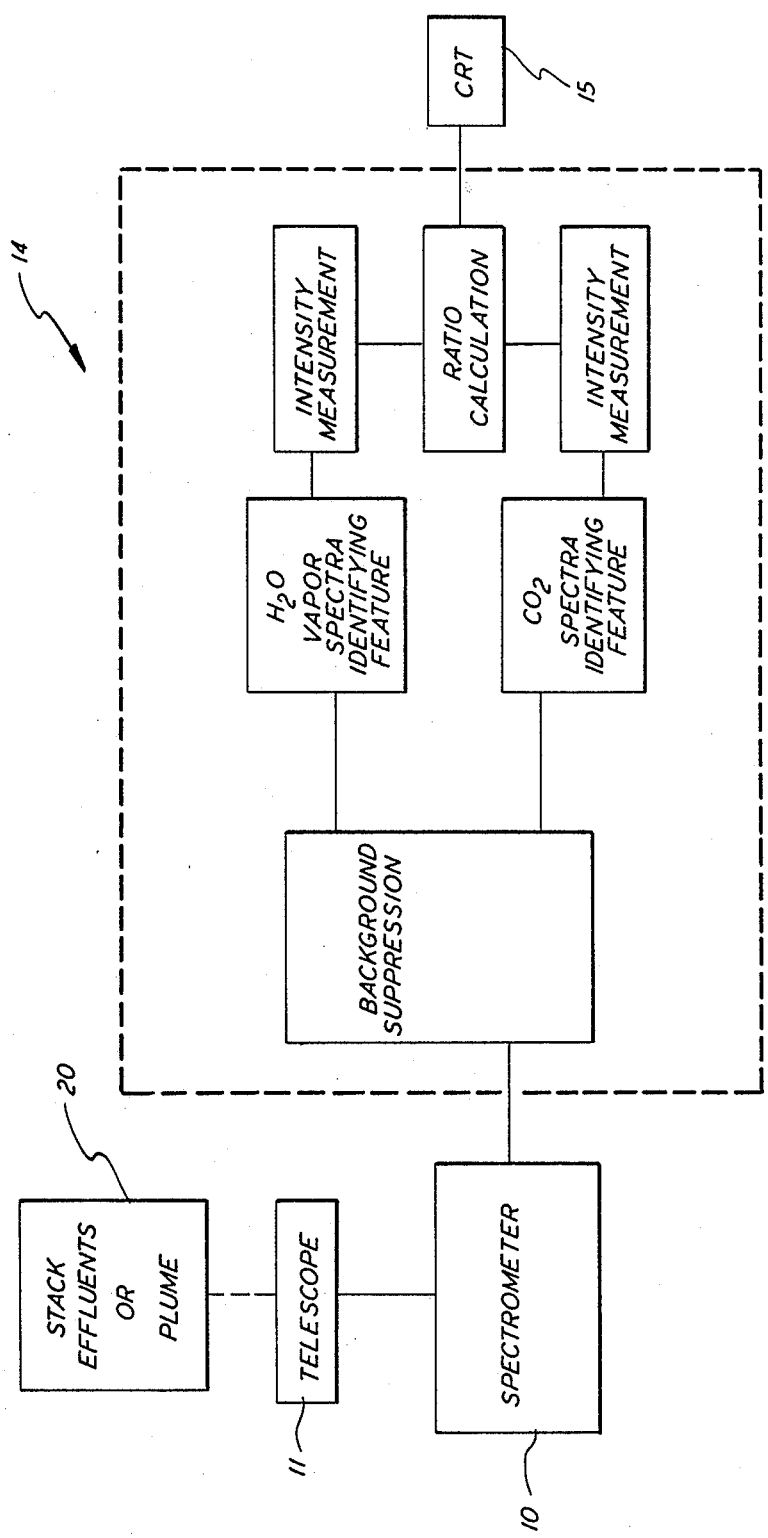
FIG. 2 is a block diagram illustrating the invention.

FIG. 2 is a block diagram representing the present invention. Stack effluents, or plume, 20 are remotely viewed by telescope 11 attached to spectrometer 10.

The spectral data from spectrometer 10 is input into computer 14. The background is suppressed and water vapor and carbon dioxide features are identified. The ratio of the intensity of the water vapor and carbon dioxide features is calculated, resulting in the discrimination between gas or oil fuel being burned. The output can be shown on CRT 15.

Figure 3:
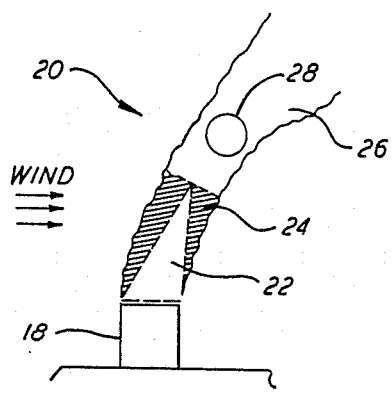
FIG. 3 is a pictorial representation of a stack showing the field of view.

In FIG. 3, the preferred position of the field of view of the spectrometer is illustrated. Plume 20 emanating from stack 18 is composed of several sections. The unmixed core 22 and sheer mixing layer 24 are between the forced plume 26 and stack 18. The field of view 28 of the spectrometer is preferably placed on the forced plume 26 during spectral readings taken for the effluents 20.

In operation, the optical site or eyepiece 12 is used to align the field of view 28 onto plume 20. Spectral readings of the target are then taken and recorded. These target spectra include the undesired time varying spectra of background objects. The unwanted spectra must be removed in order to obtain the desired spectra of the plume 20. Various background suppression techniques can be used to eliminate this unwanted background spectra. In order to remove the background spectra it is necessary to obtain a set of background spectra free of the plume spectra. This has been done by recording spectral data with the field of view 28 of spectrometer 10 outside of the plume 20 region. This was done by using two methods. One method resulted in a set of background spectra taken near in time to the time the target spectra were taken. The second method resulted in a global set of background spectra created from background spectra taken at various times, which may encompass a period of one or two days. This second set of global background spectra is preferred because it has proven to work well in suppressing the background spectra. The global background set is also easier to use, avoiding the necessity of obtaining new background spectra each time a target spectrum is taken.

The target spectrum and the global background spectra are processed by computer 14 to suppress the background and obtain a spectrum for the plume only, which is denoted a residual spectrum. Several background suppression techniques have been used to obtain the plume spectra. Two pixel differencing, three pixel differencing, and background suppression based upon factor analysis and rank annihilation algorithms have been tried with varying degrees of success. It has been found that the use of the last named technique has provided the best background suppression. The basic techniques which employ factor analysis and rank annihilation are summarized in *Chemometrics* by Sharaf, M. A.; Illman, D. L.; and Kowalski, B. R., published by John Wiley and Sons, New York, in 1986.

After the target spectrum is processed, using an appropriate background suppression technique, the residual spectrum must be analyzed. The background suppression techniques cannot remove all of the unwanted background spectra. Therefore, some unsuppressed background is present in the processed residual spectra. The identifying feature for carbon dioxide and water must be selected carefully so as to avoid the unsuppressed background components in the residual spectra.

Strong carbon dioxide features can be found at wavenumbers 719, 740, and 790 $cm^{-1}$. Strong water vapor features can be found at wavenumbers 1260–1340 $cm^{-1}$. While a variety of these features could be used to distinguish oil from gas combustion, it has been found that the carbon dioxide identifying feature located at wavenumber 719 $cm^{-1}$ provides the most reliable results. It has also been discovered that the identifying feature for water vapor located at wavenumber 1314.5 $cm^{-1}$ provides the most reliable results.

Figure 4:
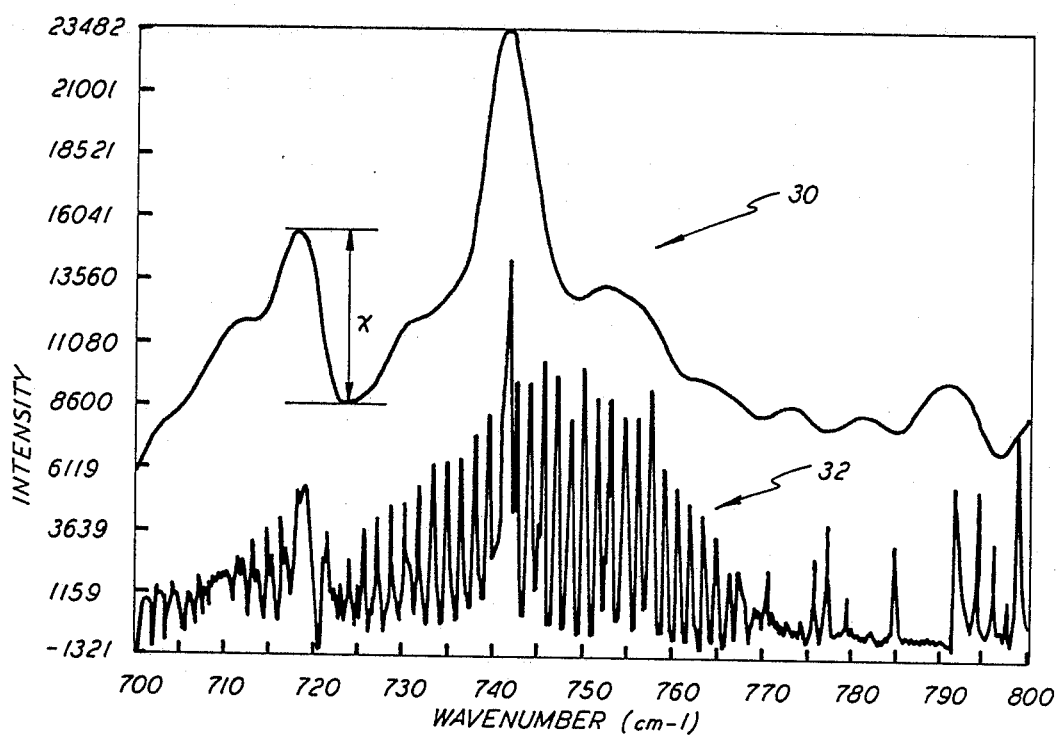
FIG. 4 is a graph showing a portion of the spectra for identifying carbon dioxide, of the plume or effluents from a sample stack.

FIG. 4 is a portion of the plume spectrum identifying a carbon dioxide feature. The vertical axis represents the intensity, and the horizontal axis represents the wavenumber. Line 30 represents a low resolution spectrum for carbon dioxide. Line 32 represents a high resolution spectrum for carbon dioxide. As can be seen in FIG. 4, the vertical line x measures the intensity of the identifying feature located at wavenumber 719 for carbon dioxide. This measured distance x is later ratioed with the identifying feature for water vapor.

Figure 5:
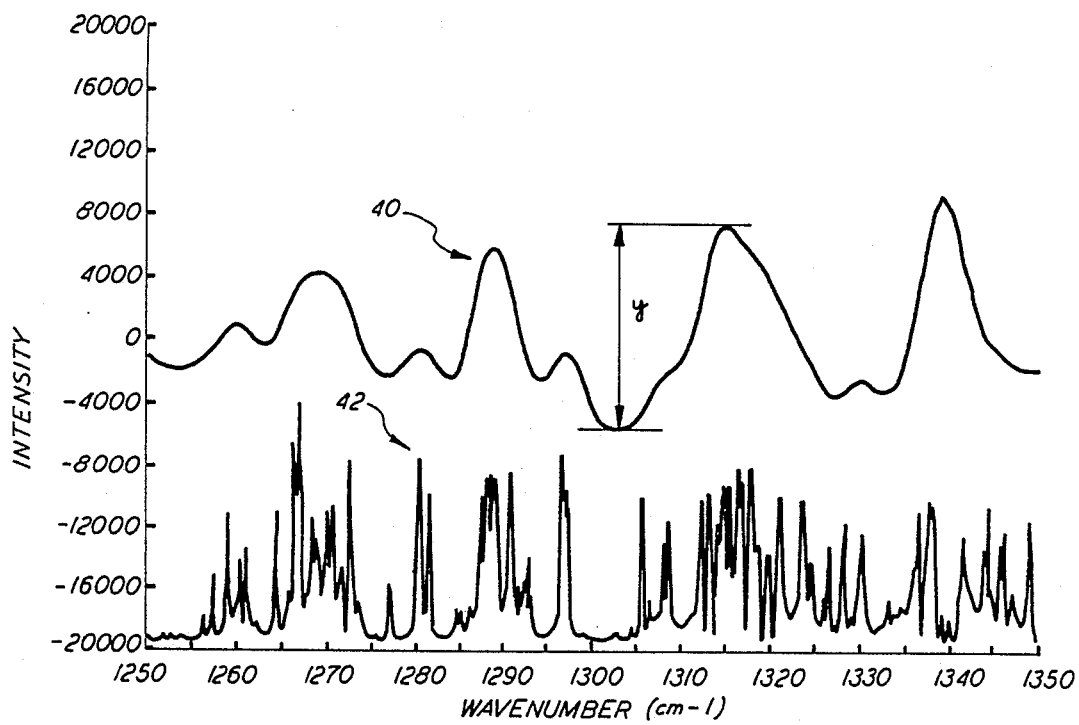
FIG. 5 is a graph showing a portion of the spectra for identifying water, of the plume or effluents from a sample stack.

FIG. 5 is a portion of the spectrum showing identifying features for water. Line 40 represents the low resolution spectrum. Line 42 represents the high resolution spectrum. The vertical axis represents the intensity, and the horizontal axis represents the wavenumber. As can be seen in FIG. 5, the vertical distance y measures the intensity of the water identifying feature located at wavenumber 1314.5. The intensity represented by the distance y is ratioed with the intensity represented by the distance x, in FIG. 4, to distinguish the burning of oil or gas fuels.

Figure 6:
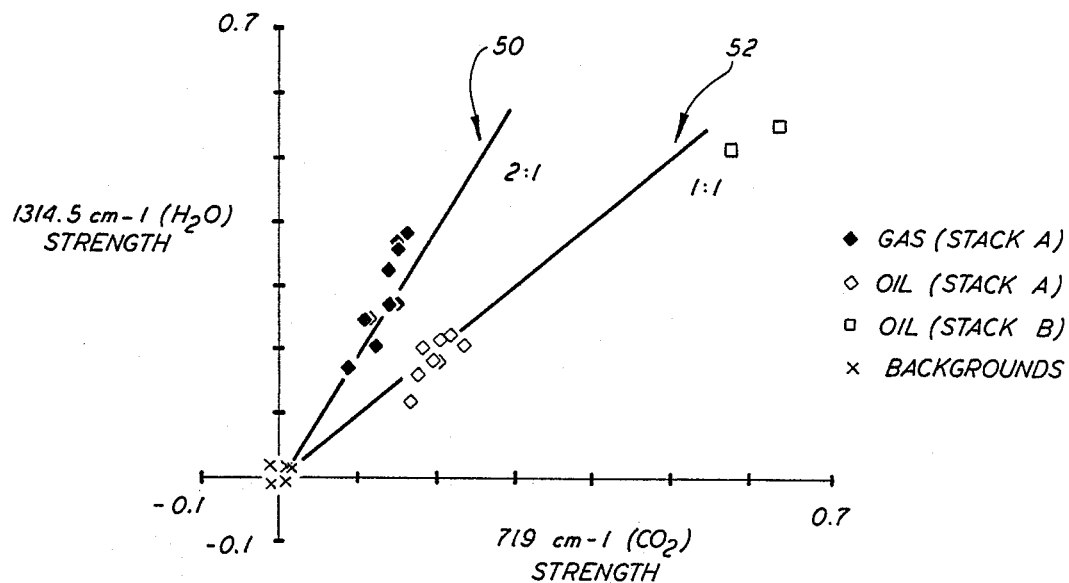
FIG. 6 is a graph illustrating the results obtained with the present invention.

FIG. 6 is a graph illustrating the results of measurements taken with the apparatus and method of the present invention. The vertical axis represents the intensity or strength of the identifying feature for water vapor located at wavenumber 1314.5. The horizontal axis represents the strength or intensity of the identifying feature for carbon dioxide located at wavenumber 719. Line 50 represents data measured from the spectra of the effluents of gas combustion. Line 50 has a slope of approximately two. Line 52 represents the data measured from the spectra of the effluents of oil combustion. Line 52 has a slope of approximately one. Due to the differing slopes, the combustion effluents of gas can be discriminated from the combustion effluents of oil. The graph of FIG. 6, or similar output, can be displayed on the screen of computer 14 so that an operator can easily determine if the plume 20 was generated by the combustion of gas or oil. Automated recording means can also be used to record the results for later viewing by an operator. Other output means can easily be devised indicating only two distinct states, gas combustion or no gas combustion.

Although the preferred embodiment has been illustrated and described, it will be obvious to those skilled in the art that various modifications may be made without departing from the spirit and scope of this invention.

What is claimed is:

1. A device for passively and remotely distinguishing between effluents from the combustion of oil or gas comprising:

spectra detecting means for detecting the infrared spectral radiation emitted by the combustion effluents;

carbon dioxide identifying means for identifying a feature characteristic of carbon dioxide from the detected spectral radiation emitted by the combustion effluents;

water vapor identifying means for identifying a feature characteristic of water vapor from the detected spectral radiation emitted by the combustion effluents;

measuring means for relativistically measuring the intensity of the feature characteristic of carbon dioxide;

measuring means for relativistically measuring the intensity of the feature characteristic of water vapor;

calculating means for calculating the ratio of the measured intensities of the features characteristic of carbon dioxide and water vapor; and output means for displaying the results of the calculating means whereby the effluents can be determined to have been generated by the combustion of gas or oil.

2. A device for remotely distinguishing between effluents from the combustion of oil or gas as in claim 1 further comprising:

background suppression means for suppressing time varying background radiation.

3. A device for remotely distinguishing between effluents from the combustion of oil or gas as in claim 1 further comprising:

a telescope directing the infrared spectral radiation to said spectra detecting means.

4. A device for remotely distinguishing effluents from the combustion of oil or gas as in claim 1 wherein:

said spectrum detecting means comprises an infrared spectrometer.

5. A device for remotely distinguishing effluents from the combustion of oil or gas as in claim 1 wherein:

said carbon dioxide identifying means identifies the spectral emission characteristic of carbon dioxide over a relatively narrow portion of the spectral emissions; and said water vapor identifying means identifies the spectral emissions characteristic of water vapor over a relatively narrow portion of the spectral emissions.

6. A device as in claim 5 wherein:

the relatively narrow portion of identifying spectral emissions characteristic of carbon dioxide is between the wavenumbers 625 and 725 $cm^{-1}$; and the relatively narrow portion of identifying spectral emissions characteristic of water vapor is between the wavenumbers 1300 and 1400 $cm^{-1}$.

7. A device as in claim 5 wherein:

the relatively narrow portion of identifying spectral emissions characteristic of carbon dioxide is located near the wavenumber 719 $cm^{-1}$; and the relatively narrow portion of identifying spectral emissions characteristic of water vapor is located near the wavenumber 1314.5 $cm^{-1}$.

8. A method for passively and remotely distinguishing effluents from the combustion of oil or gas comprising the steps of:

detecting the infrared spectral radiation emitted by the exhaust;

identifying a portion of the spectral emissions characteristic of carbon dioxide;

relativistically measuring the spectral emissions characteristic of carbon dioxide over a relatively narrow band;

identifying a portion of the spectral emissions characteristic of water vapor;

relativistically measuring the spectral emissions characteristic of water vapor over a relatively narrow band;

calculating the ratio of the relativistically measured values of the spectral emissions characteristic of carbon dioxide and water vapor;

indicating the combustion of oil or gas depending on said ratio.

9. The method as in claim 8 further comprising the step of:

suppressing the background radiation after said step of detecting the infrared spectral radiation emitted by the exhaust.

10. The method as in claim 8 wherein:

the portion of spectral emissions characteristic of carbon dioxide identified is between the wavenumbers 625 to 725 $cm^{-1}$; and the portion of spectral emissions characteristic of water vapor identified is between the wavenumbers 1300 and 1400 $cm^{-1}$.

11. The method as in claim 10 wherein:

the portion of spectral emissions characteristic of carbon dioxide identified is located near the wavenumber 719 $cm^{-1}$; and the portion of spectral emissions characteristic of water vapor identified is located near the wavenumber 1314.5 $cm^{-1}$.

12. A method for passively and remotely distinguishing between effluents from the combustion of oil or gas comprising the steps of:

detecting the infrared spectral radiation emitted by a forced plume of effluent emanating from a stack;

suppressing background spectra using factor analysis and rank annihilation techniques to obtain a residual spectrum;

relativistically measuring a portion of the residual spectrum characteristic of carbon dioxide located substantially at wavenumber 719 $cm^{-1}$;

relativistically measuring a portion of the residual spectrum characteristic of water vapor located substantially at wavenumber 1314.5 $cm^{-1}$;

calculating the ratio of the relativistically measured values of said spectral characteristic of carbon dioxide and water vapor;

comparing said ratio to a predetermined value for determining whether the combustion of oil or gas has occurred; and displaying the results of said comparing step.

* * * * *